United States Patent [19]

Spiegel et al.

[11] Patent Number: 5,089,263
[45] Date of Patent: Feb. 18, 1992

[54] NEMATICIDAL STRAIN OF PSEUDOMONAS AND ITS USE AS A BIOCONTROL AGENT

[75] Inventors: Itzhak Spiegel, Rishon-Le Zion; Ilan Chet, Nes-Ziona; Eli Cohn, Tel-Aviv; Sergio Galper, Rehovot, all of Israel

[73] Assignee: Yissum Research Development Company of the Hebrew University of Jerusalem, Jerusalem, Israel

[21] Appl. No.: 389,380

[22] Filed: Aug. 4, 1989

[30] Foreign Application Priority Data

Aug. 9, 1988 [IL] Israel ..................................... 87388
May 11, 1989 [IL] Israel ..................................... 90260

[51] Int. Cl.$^5$ ........................ A01N 63/00; C12N 1/20
[52] U.S. Cl. .................................. 424/93; 435/253.3; 435/874
[58] Field of Search ............ 424/93; 435/252.1, 253.6, 435/253.3, 254, 874

[56] References Cited

U.S. PATENT DOCUMENTS 4,536,207  8/1985  McCandliss et al. ................. 530/350
4,751,081  6/1988  Suslow et al. ......................... 424/93

FOREIGN PATENT DOCUMENTS 203708   12/1986  European Pat. Off. .
0217378   4/1987  European Pat. Off. .
58-24508   2/1983  Japan .
WO85/01878  5/1985  World Int. Prop. O. .

OTHER PUBLICATIONS

Commonwealth Agricultural Bureau, 1983, Abstract No. 83994666, Slaugh, GB; I. H. Mian et al.
Biological Abstracts, vol. 78, No. 6, 1984, Abstract No. 46568, Biological Abstracts, Inc., G. Godoy et al.
Biological Abstracts, vol. 84, No. 1, 1987, Abstract No. 8590, Biological Abstracts, Inc., A. K. Culbreath et al.
Biological Abstracts, vol. 86, No. 9, Abstract No. 95935, Biological Abstracts, Inc., Y. Spiegel et al.
Japanese Patents Gazette, Section CH, week 8644, 10th Dec. 1986, Derwent Publications Ltd.
Spiegel et al, "Use of chitin for controlling plant parasitic nematodes", 1986, 87-95.
Spiegel et al, "Use of chitin for controlling plant plant-parasitic nematodes", 1987, 337-345.
Spiegel et al, "Use of chitin for controlling plant-parasitic nematodes", 1988, 251-256.
Spiegel et al, "Evaluation of a protein-chitin derivative of crustacean shells as a slow-release nitrogen fertilizer on Chinese Cabbage", 1988, 621-627.
Spiegel et al, "Use of Chitin for Controlling Heterodera avenae and tylenchulus semipenetrans", 1989, 419-422.

Primary Examiner—Douglas W. Robinson
Assistant Examiner—Carol Geckle
Attorney, Agent, or Firm—Foley & Lardner

[57] ABSTRACT

Microorganisms isolated from soil enriched with chitin or collagen were found to be very effective in controlling soil nematodes, probably by destroying their eggs or egg-shells. Pure culture of such microorganisms were prepared. These microorganisms are formulated into solid or liquid nematicidal compositions and as such used for combating soil-nematode infestations.

9 Claims, 6 Drawing Sheets

NEMATICIDAL STRAIN OF PSEUDOMONAS AND ITS USE AS A BIOCONTROL AGENT

FIELD OF THE INVENTION

The present invention is in the field of biological control of pests and more specifically concerns the use of micro-organisms isolated from a chitin or collagen enriched soil as bionematicides.

BACKGROUND OF THE INVENTION AND PRIOR ART

In recent years there has been a growing interest in biological control of agricultural pests, in view of the hazardous environmental effects of conventional chemical pesticides. Such a control has the advantage of being target specific and not polluting the environment.

One of the major pests which infect agricultural crops are nematodes. Thus, a non pollutant and effective method for controlling this pest would be most desirable.

The use of nematode eating bacteria for controlling nematodes infestation such as root-knot nematodes, root lesion nematodes and cyst nematodes, has been disclosed in J-A1-58-024508. According to this published patent application, a solution containing nematode-eating bacteria is impregnated into porous materials such as vermiculite, pearlite, zeolite or peat moss, and the so impregnated porous material is added to the plants environment.

Inhibition of nematodes and fungi infestations of plants by certain strains of rhizobacteria, has been disclosed in EP-A1-160089. According to this published patent application, protection against nematodes can be obtained either by introducing such bacteria into the plant rhizosphere or inoculating seeds with a solution containing these bacteria prior to seeding thereof into the ground. The inhibition by these strains of bacteria, is especially effective in the presence of assimilate nitrogen carbon sources.

A synergistic nematicidal composition comprising a carbamate or dithiocarbamate nematocide together with *Pasteuria penetrans* bacteria has been disclosed in EP-A1-217,378.

SUMMARY OF THE INVENTION

In accordance with the present invention micro-organisms isolated from chitin or collagen enriched soil were found to be very effective in controlling soil nematodes probably by destroying their egg-shells or egg sacs. It has, moreover, been surprisingly found, in accordance with the invention, that a growth medium in which said micro-organisms were raised and from which they were recovered, a supernatant, a homogenate, or an extract thereof, as well as solid products obtainable from such supernatant, homogenate or extract can also be effective in controlling soil nematodes. Such supernatants, homogenate extracts and solid products will be referred to hereinafter collectively as "residual medium" and "residual media".

Thus, the present invention provides a method of combating soil nematodes comprising introducing into the soil an effective amount of nematicidal micro-organisms isolated from soil enriched with chitin or collagen and/or of a residual medium.

The present invention also provides a nematicidal composition for use in plant protection, comprising as active ingredient an effective amount of the abovementioned nematicidal micro-organisms and/or a residual medium as herein defined, together with a carrier compatible with said active ingredient and with the soil environment.

The invention further provides a method of preparing a pure culture of nematicidal micro-organism, comprising artificially enriching soil with chitin or collagen, allowing the micro-organisms to proliferate in such soil, admixing a micro-organism bearing soil sample with either chitin or collagen (depending on the type of soil enrichment) to produce a growth mixture with the chitin or collagen as essentially the sole carbon source, incubating said growth mixture to induce micro-organismal growth, subjecting the so obtained micro-organismal culture to purification procedures known per se.

Several types of nematicidal micro-organisms were isolated in accordance with the present invention from soil enriched either with chitin or collagen. Examples of such micro-organism isolated from chitin enriched soil are bacteria of the genera Pseudomonas and Aeromonas. Examples of such micro-organisms, isolated from a collagen enriched soil are fungi of the genus Cunninghamella particularly from the species *C. elegans*.

Several strains of these micro-organisms have been obtained in pure culture form. The following may be mentioned in particular:

(i) A strain which was termed "20M", of a yet unidentified bacterial species of *Pseudomonas*. This strain was deposited on Oct. 10, 1988 at the Institute Pasteur, Collection Nationale de Cultures de Micro-organismes (C.N.C.M) and was accorded the designation I-804.

(ii) A mutant strain of 20M which was termed "20M-2".

(iii) A strain which was termed "2F" of a yet unidentified bacterial species of the genus *Aeromonas*.

(iv) A strain which was termed "30CE" of the species *C. elegans* from the fungal genus *Cunninghamella*.

The present invention thus further provides pure cultures of nematicidal micro-organisms, isolated from a chitin or collagen enriched soil. Particularly the present invention provides such pure cultures of the strains 20M, 2F and 30CE.

Also provided by the present invention are nematicidal methods and composition utilizing the abovementioned three micro-organismal strains.

The so obtained pure cultures are grown and conserved in media comprising chitin or collagen as a carbon source, but other carbon sources such as glucose may also be present. The pure cultures may be stored for long periods of time by freezing or freeze drying.

Pure cultures according to the present invention may be mutated in a controlled manner by subjecting them to the action of various mutagens, such as radioactive substances, chemical mutagens, and irradiation by γ- or X-rays, in order to obtain a new mutant strain with improved nematicidal capability or other improved properties such as improved viability, susceptibility to storage, high growth rate and the like. Accordingly, the term "pure cultures of nematicidal micro-organisms" used herein applies to both a parent strain of nematicidal micro-organisms as first obtained in pure culture form and a nematicidally active mutant thereof.

In accordance with the present invention the nematicidal micro-organisms or the residual medium are applied to the soil or added into a pot-mix in order to prevent a nematode infestation or to inhibit the spread of such an infestation after its occurrence. For the application of these micro-organisms or the residual medium to the soil it is possible to formulate them in a liquid composition, which may be sprayed, incorporated into the irrigation water or used for the impregnation of seeds or roots before sowing or planting, respectively. They may also be formulated in dry compositions together with solid carriers, and admixed into the soil in this form.

For commercial purposes, large quantities of nematicidal micro-organisms are required in order to prepare agricultural composition comprising these. Such large quantities are best obtained by a fermentation process that comprises inoculating a sample of a micro-organismal culture of the kind specified, preferably in pure culture form, into a fermentation tank containing a fermentation medium which includes chitin and/or collagen as the case may be and other nutrients. The fermentation is carried on until a sufficient concentration of the micro-organism is achieved, e.g. about $10^{10}$ cells/ml in the case of bacteria and about $10^7$ cells/ml in the case of fungi. As a rule, for industrial scale fermentation of nematicidal micro-organisms, unpure and thus cheap sources of chitin which contain also proteins other than chitin may be used.

If the culture of the nematicidal micro-organisms is contaminated, e.g. with other bacteria, the resulting ferment will comprise large quantities of non-nematicidally active bacteria, which in some cases may even be in abundance. This will bring about a reduction of the effectiveness of the compositions which will be prepared from this ferment. Accordingly, it is preferred to utilize pure cultures for fermentation.

The so obtained fermentation broth may be employed as is, as a liquid nematicidal composition of nematicidal micro-organisms for use in plant protection. Alternatively, the liquid composition may be prepared by transferring the micro-organisms to another medium compatible with both the micro-organisms and the soil environment.

Dry formulations of nematicidal micro-organisms are prepared, for example, by impregnating the so-obtained fermentation broth into a porous solid carrier which is then dried. However, care must be taken that the micro-organisms remain viable even after a prolonged storage or after long periods of time in the ground and this may be achieved by various appropriate additives. Moreover, the said carrier used should preferably be poor in nutrients so as to avoid growth of other types of micro-organisms thereon.

DETAILED DESCRIPTION OF THE INVENTION

In the following description and Examples the following terms will be used:

"chitinolytic bacteria"—to denote bacteria isolated from soil enriched with chitin;

"collagenolytic bacteria"—to denote bacteria isolated from soil enriched with collagen;

"chitinolytic fungi"—to denote fungi isolated from soil enriched with chitin;

"collagenolytic fungi"—to denote fungi isolated from soil enriched with collagen.

However, it should be noted that these terms do not mean to imply that chitinolytic bacteria as defined herein possess only chitinolytic activity and not, for example, collagenolytic activity. On the contrary, some chitinolytic bacteria as defined herein may possess also collagenolytic activity which some time may even be stronger than its chitinolytic activity. The same applies also to chitinolytic fungi and vice-versa also to collogenolytic bacteria or fungi. Additionally, it was found that all micro-organisms isolated in accordance with the invention showed a substantial general proteolytic activity.

In the following, reference will at times be made specifically to chitinolytic bacteria, it being understood that the same applies also, *mutatis mutandis*, to collagenolytic bacteria, as well as to chitinolytic and collagenolytic fungus.

Where appropriate, the important differences which apply to the other micro-organisms, will at times be indicated.

I. Formulation of nematicidal micro-organisms

The nematicidal micro-organisms may be formulated into a dry or a liquid composition. A dry composition comprises as a rule a solid carrier that is compatible with the micro-organismal population and with the soil environment. The carrier serves both to preserve micro-organismal viability, and also to enable the micro-organismal proliferation upon application to the soil. The carrier should further not interfere with the interaction between the bacteria and their target (i.e. nematode eggs or egg sacs in the rhizosphere). A suitable carrier is one made of a porous material, optionally together with additives that serve as adherents.

A dry composition of the nematicidal micro-organism is generally prepared by contacting particles of the solid carrier with liquid suspension of the micro-organisms for a sufficient time for the particles to become impregnated with the micro-organismal suspension. Thereafter the carrier is separated from the liquid and dried. Optionally various additives such as adherents may be added prior to drying the impregnated carrier.

A dry composition of nematicidal micro-organisms according to the invention may be supplied to soil by conventional methods. For example, the composition may be spread in a field (the whole area or parts thereof) by means of a sowing machine or by apparatus conventionally used for spreading of dry fertilizer. The dry composition may also be included in pot soil mixtures.

Introduction of the nematicidal micro-organisms into the soil may also be in the form of a liquid composition e.g., by spraying such a composition directly onto the area to be treated or by incorporating an *a priori* dry or liquid composition in irrigation water, in a similar manner as conventionally used for introducing fertilizers. Aqueous compositions of nematicidal micro-organisms for spraying may be a micro-organismal suspension obtained by fermentation as is, or a dilution thereof, or may be prepared from a dry pure culture or solid composition by the addition of water or an aqueous solution.

A medium in which nematicidal micro-organisms were grown and from which they were recovered also possess nematicidal activity. Accordingly, such a medium may be used as is as a nematicidal composition, or may be processed in a manner known per se, into aqueous or dry products with nematicidal activity. As mentioned above, such residual media are effective nematicidal agents and are applied in a similar manner as the bacteria proper.

Liquid compositions of nematicidal micro-organisms and/or residual media may also be used to impregnate seeds or plant roots prior to seeding or planting, respectively.

The composition should preferably also be capable of inducing micro-organismal proliferation upon introduction into the soil. For that purpose it is useful to add also a nutrient source such as cotton seed meal, collagen and/or chitin as the case may be, and the like. While in principle, the addition of nutrients to the composition may be performed in advance, it should be noted that early introduction is practical only in a dry composition and even then care must be taken to avoid proliferation of undesired contaminating micro-organisms.

II. Preparation of a pure culture of nematicidal micro-organisms

Pure cultures according to the present invention are obtained from soil artificially enriched with either chitin or collagen. Such soil enrichment promotes the proliferation of chitinolytic or collagenolytic bacteria and fungi, many of which are effective in controlling soil nematodes.

The enriched soil may either be in an open plot or within an enclosure such as a hot house, various kinds of containers, pots and the like. One suitable source of chitin for that purpose are various chitin rich waste products such as those obtained from ground crustacean shells and the like. One suitable source of collagen may, for example be the kind which is used in the meat industry. Where the chitin or collagen source is spread on the soil, a suitable amount thereof is about 15-20g/m$^2$. Where, on the other hand, the chitin or collagen source is admixed with soil, e.g. for use as a pot mixture, a suitable amount is about 0.01-0.05% by weight (w/w).

Reference will hereinafter be made specifically to the preparation of a pure culture of chitinolytic bacteria.

Once the chitinolytic bacteria have proliferated in the chitin enriched soil, samples of this soil are collected and inoculated into a selection medium comprising chitin as the sole carbon source. For this purpose it is necessary to use pure chitin so as to avoid growth of non-chitinolytic bacteria. A suitable pure source of chitin is, for example, colloidal chitin such as that manufactured by Sigma, MO., U.S.A., and which may also be prepared by methods known per se. In addition to chitin the selection medium should contain also a nitrogen source, such as $KNO_3$, certain ions such as $Na^+$, $K^+$, $Mg^{+2}$ $PO_4^{-3}$ and $SO_4^{-2}$, and a buffer to keep the pH at about 6-8 preferably 6.5-7.5.

After incubation for a period sufficient for the bacteria to proliferate, a sample of the medium is transferred to another selection medium having essentially the same compositions for an additional selection stage. Thus, for example, where the selection medium is an agar medium, single colonies of bacteria may be suspended in a liquid solution and after a sufficient dilution seeded on agar.

The selection stages may be repeated several times until a pure culture is obtained.

The isolation procedure of pure cultures of collagenolytic bacteria is very similar, replacing, however chitin in each stage with collagen.

The procedure for isolating fungi is also very similar, the essential difference being the medium used for growing the fungi which should be appropriate for fungal growth. A suitable medium may for example be "Martin-Rose Bengal Medium" comprising chitin or collagen as a carbon source but as distinct from the medium used for the isolation of the bacteria, the medium here comprises also another carbon source such as glucose.

III. Conservation of the culture

Pure cultures of chitinolytic bacteria obtained according to the invention, may be conserved in a culturing vessel containing a medium which provides at least the minimal requirements for the bacteria's survival and growth. This medium may in principle be any bacterial growth medium known in the art but in order to suppress growth of contaminating micro-organisms it is preferable to utilize a growth medium comprising chitin as the major carbon source. This medium may thus be similar to the selection medium, but the chitin source need not necessarily be pure. In order to keep the micro-organisms always in their growth phase, samples of the culture should be transferred once in a while into a new medium. e.g. once every two weeks.

It should be noted that such conservation of the culture is only suitable for a relatively short period, i.e. for several weeks to several months. Conservation of the culture for longer periods, i.e. months to years is laborious since repetitive transfers are necessary every few days. Additionally, there always exists the possibility of contamination by other micro-organisms even if utmost care is taken. Furthermore, with time, spontaneous mutations may occur which may change the culture's properties in an uncontrolled manner.

Pure cultures of collagenolytic bacteria may be conserved in a similar manner replacing however chitin with collagen.

Fungal cultures in accordance with the invention may be conserved for a time in media which are suitable for fungal growth and proliferation. An example of such a medium is an agar substrate which comprises a carbon source such as wheat-bran extract and possibly also chitin or collagen, as the case may be.

Due to the consumption of nutrients by the fungal cells and the secretion of waste products, samples thereof comprising either cells or conidia produced thereby should be transferred regularly into new, fresh media. For example, if the culture is growing on agar substrate, conidia which are produced by the fungal cells can be harvested and then seeded onto a new agar substrate. Harvesting of the conidia is suitably performed by the addition of distilled water onto the agar substrate, upon which, due to hypertonic pressure, the ripe conidia are excreted into the supernatant fluid where they can easily be collected.

From similar grounds as described above in connection with the bacteria, such a conservation is only suitable for relatively short periods of time. For storage periods of up to about 6 months, a monolayer of fungal cells on a solid matrix, such as bran extract agar, is kept at about 4° C.

Conidial suspensions on the other hand, may be stored for longer period, i.e. up to about 12 months in 4° C.

IV. Long-term storage of the culture

Long term storage may be achieved, as mentioned above, by either freezing a micro-organismal suspension or freeze drying it. In the case of chitinolytic bacteria the culture is grown for a certain time, until a logarithmic growth phase is reached. A suitable medium for such growth is a liquid colloidal chitin medium. Before freezing, a freezing mix comprising for example 80% glycerol and 20% liquid medium with colloidal chitin is admixed into the bacterial suspension. The so obtained mixed suspension is kept for some time at room temperature, e.g. for 30 minutes, and then frozen to about −70° C.

For freeze-drying, the chitinolytic bacteria may be grown in a liquid colloidal chitin medium until a logarithmic growth phase is reached. The bacterial suspension is then centrifuged, e.g. at 12000 g for 10 min. The bacterial pellet which is obtained after removal of the supernatant is suspended with 10% skimmed-milk powder, and the suspension is mixed thoroughly, e.g. by a vortex. The so-mixed suspension is frozen in dry ice-acetone and then lyophilized.

Thawing or rehydrating the bacteria is performed by methods known per se.

Long term storage of the other micro-organisms of the invention is performed in a similar manner, with various modifications obvious to the man of the art.

V. Fermentation

Fermentation is required in order to obtain large quantities of micro-organisms for the purpose of preparing agricultural nematicidal compositions of these micro-organisms. The fermentation medium will generally comprise a carbon source and other ingredients needed for the micro-organismal growth and proliferation. However, in order to avoid growth of contaminating non-nematicidal micro-organisms it is preferable to use as a carbon source, at least as the major one, either chitin or collagen, depending on the specific micro-organism. In the following the fermentation will be described with respect to chitinolytic bacteria.

The fermentation medium for obtaining large quantities of chitinolytic bacteria will preferably include chitin as a carbon source e.g. a chitin rich waste product such as crude ground crustacean shells (hereinafter "crude chitin"), and may also include additional carbon sources such as glucose. Preferably the fermentation medium also includes buffering salts, yeast extract, glucose and a nitrogen source such as $KNO_3$.

In such a fermentation medium, care must be taken that no factor will become limiting, and various parameters such as pH, mineral strength, temperature and the like, should be kept within tolerance limits of the bacteria and preferably at optimal levels.

The optimal pH for fermentation was found to be about 6.5-7.5. The optimal concentration of yeast extract was found to be between about 0.1% to about 0.4% (w/v). The preferred concentration thereof being about 0.3%.

When $KNO_3$ is used as a nitrogen source, its optimal concentration in such a medium was found to be from about 0.05% to about 0.2%, with about 0.1% being preferred. Glucose, although not an essential constituent, was found to have a positive effect on the growth of the bacteria. The optimal concentration range of glucose was found to be about 0.1% to 0.4%, about 0.2% being preferred. When crude chitin is used as a chitin source, its preferred concentration range is from about 0.1% to 0.4%, about 0.2% being preferred. The growth of these bacteria was found to be sensitive to the buffering salt's concentration, which should thus be kept below about 0.01M, the preferred concentration being about 0.008M.

When optimal conditions are kept, final cell counts may reach $10^{10}$ cells/ml.

Fermentation of collagenolytic bacteria is performed in a similar manner replacing however, chitin with collagen all other conditions being about the same. A suitable collagen source is for example that which is used in the meat industry.

Fermentation of nematicidal fungus may be performed by growing the fungus in, for example various industrial waste products. Suitable fermentation media are for example, potato broth (which is the soluble extract of boiled potatoes), corn-steep liquor (which is a syrup remaining after boiling of corn seeds in the starch industry), cotton meal extract (the extracted composites of cotton seed meal following boiling), whey, wheat-bran or a combination thereof, to which collagen and/or chitin may be added. The fungi may also be fermented in a semi-solid medium, i.e. a wet particulate solid substrate, e.g. powdered carriers such as vermiculite and peat-moss or within wet granulated matrices such as of sorghum, wheat or barley grains.

Liquid fermentation is performed by innoculating a sample of the fungi into a growth medium and aerobically incubating the medium for a sufficient amount of time. The optimal temperature for fermentation was found to be about 25° C. and the optimal pH about 6.5 to about 8.0. Fermentation is preferably carried out under agitation e.g. in shaking flasks.

From the above media the preferred liquid medium for performing the fermentation of the fungal cultures is one which comprises about 20% potato broth and about 0.1% collagen and/or chitin. In this medium the yield of cells after seven to nine days incubation is about 10 fold that of the other media listed above. Additionally, it was found that a similar yield is achieved when utilizing a whey medium supplemented with corn steep liquor with the relative volume of whey to corn steep liquor being about 2:1.

Semi-solid fermentations may be carried out on a number of carriers as specified above. The final number of fungi cells which can be harvested after such fermentation is higher than that achieved with liquid fermentation, although the fermentation time, which depends on the carrier type, is usually longer.

DESCRIPTION OF SOME SPECIFIC EMBODIMENTS

In the following description some examples and tests are described, which are meant to illustrate the present invention, it being understood that the invention is not restricted to these examples and that within the scope of the invention defined in the claims, modifications are possible as will readily be understood by persons versed in the art.

Furthermore, the following examples refer specifically to pure cultures of the bacterial strains 20M and 2F and to the fungal strain 30CE which are novel products and an aspect of the present invention. It should however be understood that similar results are obtainable with other bacterial strains that are within the scope of the claims.

DESCRIPTION OF THE DRAWINGS

In the following description reference will at times be to the annexed drawings in which.

EXAMPLE 1

Isolation of 20M and 2F

50ml pots were filled with a natural sandy soil mixed with 0.2% (w/w) Clandosan. The pots were incubated for up to 45 days in a temperature controlled greenhouse (27-29° C.), the soil being kept moistened throughout the whole incubation period. Four pots were removed daily and 20g soil samples from each pot were stored at 5° C. until subjecting them to processes for the isolation of chitinolytic bacteria.

For isolation of chitinolytic bacteria samples of 10g of soil were suspended in 90ml of sterile water in 250ml flasks which were then shaken for 30 min in a rotating shaker. Decimal dilutions were made and 0.1ml was spread on agar plates with a salt medium containing 0.2% (w/w) chitin (Sigma, MO., U.S.A.) as the sole carbon source. Chitinolytic activity of the bacteria was evidenced by a halo around bacterial colonies, resulting from degradation of chitin. The colonies showing chitinolytic activity were isolated and processed further. Those colonies which showed the strongest chitinolytic activity (i.e. the "clearest" halo around the colonies), were further screened for nematicidal activity.

Many cultures having nematicidal activity were obtained, among those 20M and 2F, which were isolated from a soil sample removed after 20 days showed the strongest chitinolytic and the best nematicidal activity.

EXAMPLE 2

Growth medium for 20M and 2F

A suitable medium for growing the 20M and 2F culture has the following composition:

0.2% crude chitin, 0.2% glucose, 0.1% $KNO_3$, 0.1% $(NH_4)_2SO_4$, 0.03% $MgSO_4 \cdot 7H_2O$, 0.1% $KH_2PO_4$, 0.15% $K_2HPO_4$ and 0.05% yeast extract.

In this medium the optimal pH was found to be between 6.5 and 7 and the optimal temperature was found to be about 25°. This medium as is, is suitable both as a fermentation medium, and without glucose as a conservation medium.

EXAMPLE 3

Properties of 20M (a) Antibiotic sensitivity

A suspension of 20M was spread over agar plates containing the growth medium of Example 1. Discs impregnated with various antibiotics were placed on the agar plates which were then incubated for 24hrs at 30° C. The effect of antibiotics was assayed by measuring the diameter of the growth inhibition zone.

The results are shown in the following Table I:

TABLE I

| Antibiotics | Amount (mg) | Diameter of Inhibition (mm) |
|---|---|---|
| Ampicillin | 10 | 8 |
| Cephaloridin | 5 | 6 |
| Calistin sulphate | 25 | 1.5 |
| Gentamycin | 10 | 1.5 |
| Streptomycin | 10 | 1.5 |
| Sulphatriad | 200 | 12 |
| Tetracycline | 25 | 15 |
| Contrimoxazole | 25 | >15 |

(b) Chitinolytic and proteolytic activity of 20M in various fermentation stages 20M was fermented in three stages as follows:

Stage I: 20 ml of 20M suspension containing $10^6$ cells/ml were admixed into 80ml of a growth medium of Example 2, however without glucose, and incubated 24 hrs.

Stage II: The 100ml 20M suspension obtained in Stage I was transferred into 900 ml of a growth medium having the composition of Example 2, however with yeast extract elevated to 0.3%, and incubated for an additional 24 hrs.

Stage III: The 1l 20M suspension obtained in Stage II was transferred into 4l of a growth medium having the same composition as in Stage II.

Samples were withdrawn at the end of Stages II and III and were subjected to colorimetric tests for the detection of chitinolytic and proteolytic activity.

The results are summarized in the following Table II:

TABLE II

| Exp. | Fermentation Stage | Cells/ml in sample | Chitinase specific activity (U/ml/h) | Protease specific activity (U/ml/min) |
|---|---|---|---|---|
| 1 | II | $1 \times 10^9$ | 0.011 | 0.04 |
|   | III | $7.6 \times 10^8$ | 0.01 | 0.015 |
| 2 | II | $6 \times 10^9$ | 0.105 | 0.075 |
|   | III | $9.4 \times 10^8$ | 0.027 | 0.025 |
| 3 | II | $1.5 \times 10^9$ | 0.038 | 0.081 |
|   | III | $2 \times 10^9$ | — | 0.028 |
|   | III | $1.2 \times 10^9$ | — | 0.028 |
|   | III | $6 \times 10^8$ | 0.008 | 0.029 |
|   | III | $3 \times 10^9$ | 0.09 | 0.060 |
|   | III | $5 \times 10^9$ | 0.146 | 0.083 |
| 4(*) | III | $1.8 \times 10^9$ | 0.016 | 0.055 |

(*) This experiment consisted only of Stage III fermentation, i.e. the initial 20M suspension was incubated directly into a 5 l medium.

As may be seen, apart from chitinase activity, 20M possesses also a comparably strong proteolytic activity.

EXAMPLE 4

A mutant of 20M

A mutant strain of 20M has been isolated which shows resistance to rifampiicin, which resistance is apparent in the strain's ability to grow unhindered in the presence of 200μg/ml of this antibiotic. Otherwise, its properties are identical to those of 20M.

This strain, termed 20M-2, has the advantage that that antibiotic may be added into its growth medium or fermentation medium, and while this micro-organism will grow unhindered, the growth of other types of contaminating micro-organisms will be eliminated or at least minimized, without the need to observe strict serialization condition, which is a difficult and costly feat by itself.

EXAMPLE 5

Fermentation of 20M and 2F (I) 20M (a) Starter Fermentation

Into a 5 l bench top fermentor containing 5 l of a growth medium according to Example 2, 50 ml of 20M suspension was inoculated to a final concentration $10^4$ cells/ml, and the bacteria were aerobically grown for 24 hrs.

(b) Main Fermentation

The so-incubated medium of the starter fermentation was transferred to a 200 l batch fermentor containing a further amount of 200 l of the medium of Example 1 and the mixture was incubated for a further 20–24 hrs. After incubation, the cells were counted and in each case the yield was about $10^{10}$ cells/ml (II) 2F Fermentation of 2F was carried out in a similar manner as 20M and about the same cell yield was obtained.

EXAMPLE 6

Growth on Agar (I) 20M

A sample of 20M culture was grown on plates containing an agar substrate, which agar contained colloidal chitin, and further constituents as in Example 2 (except for crude chitin and glucose). After about 24 hrs the bacterial cells were counted and the cell yield was found to be $10^{10}$ cells/ml.

The chitinolytic activity of the cells was apparent by a halo around bacterial colonies.

(II) 2F 2F was grown on agar in the same manner as 20M and a similar chitinolytic activity was observed.

EXAMPLE 7

Growth of 20M in various growth media (a) Effects of chitin sources, mineral combinations and glucose Two different mineral solutions were used, one termed "C" comprising sulphates and the other termed "S" and comprising sulphates and phosphates. Into each solution either of three types of chitin was added, these three types being powdered chitin (CT), colloidal chitin (COLO), and crude chitin (CL). Glucose was supplemented into half of the tested media.

Thus, the following media were tested:
S-CT: buffer S + ground chitin;
S-CT G: buffer S + ground chitin + glucose;
S-COLO: buffer S + colloidal chitin;
S-COLO+G: buffer S + colloidal chitin + glucose;
S-CL: buffer S + crude chitin;
S-CL+G: buffer S + crude chitin glucose;
C-CT: buffer C + ground chitin;
C-CT+G: buffer C + ground chitin + glucose;
C-COLO: buffer C + colloidal chitin;
C-COLO+G: buffer C + colloidal chitin glucose.

0.1 ml of a suspension taken from a culture of 20M containing $10^7$ cells/ml was inoculated into 20 ml of each of the tested media (the initial cell concentration in the tested medium was thus about $10^5$ cells/ml). Cell numbers were counted after 6 hrs, while the cultures were in their log growth phase and after 24 hrs when the cultures were in the stationary phase. The results are graphically represented in FIGS. 1 and 2 of the annexed drawings.

Figure 1:
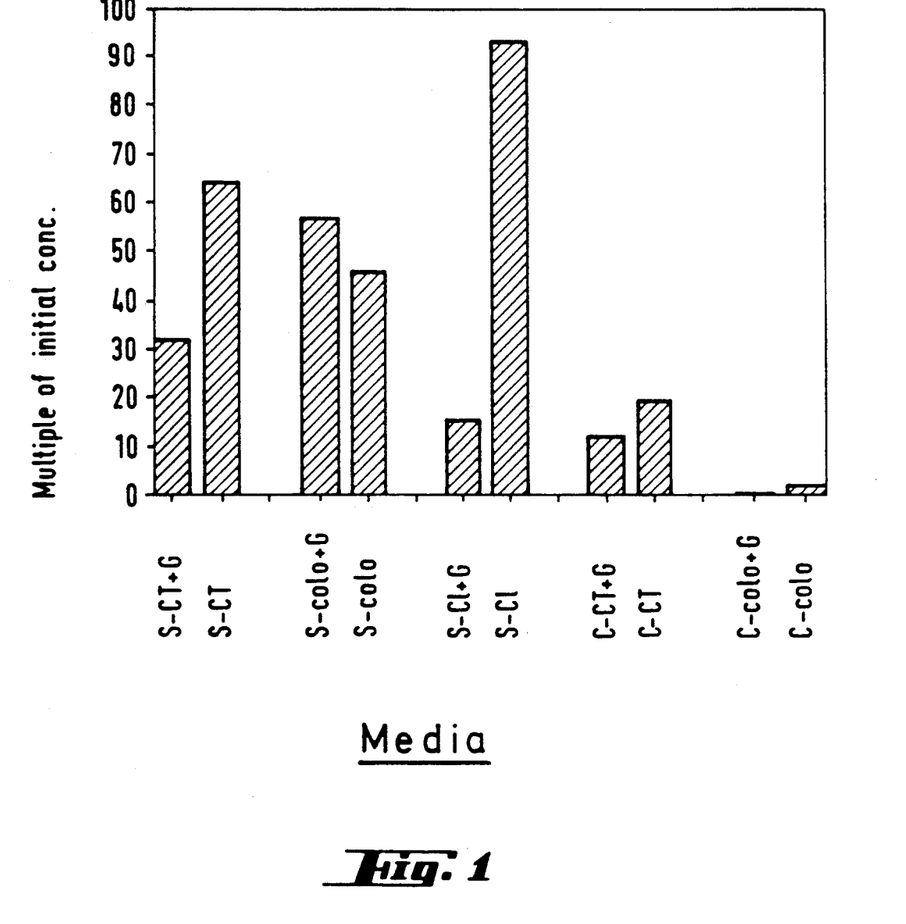
FIGS. 1 and 2 show average results of an experiment wherein the effect of different media on 20M cell proliferation was tested.
Figure 2:
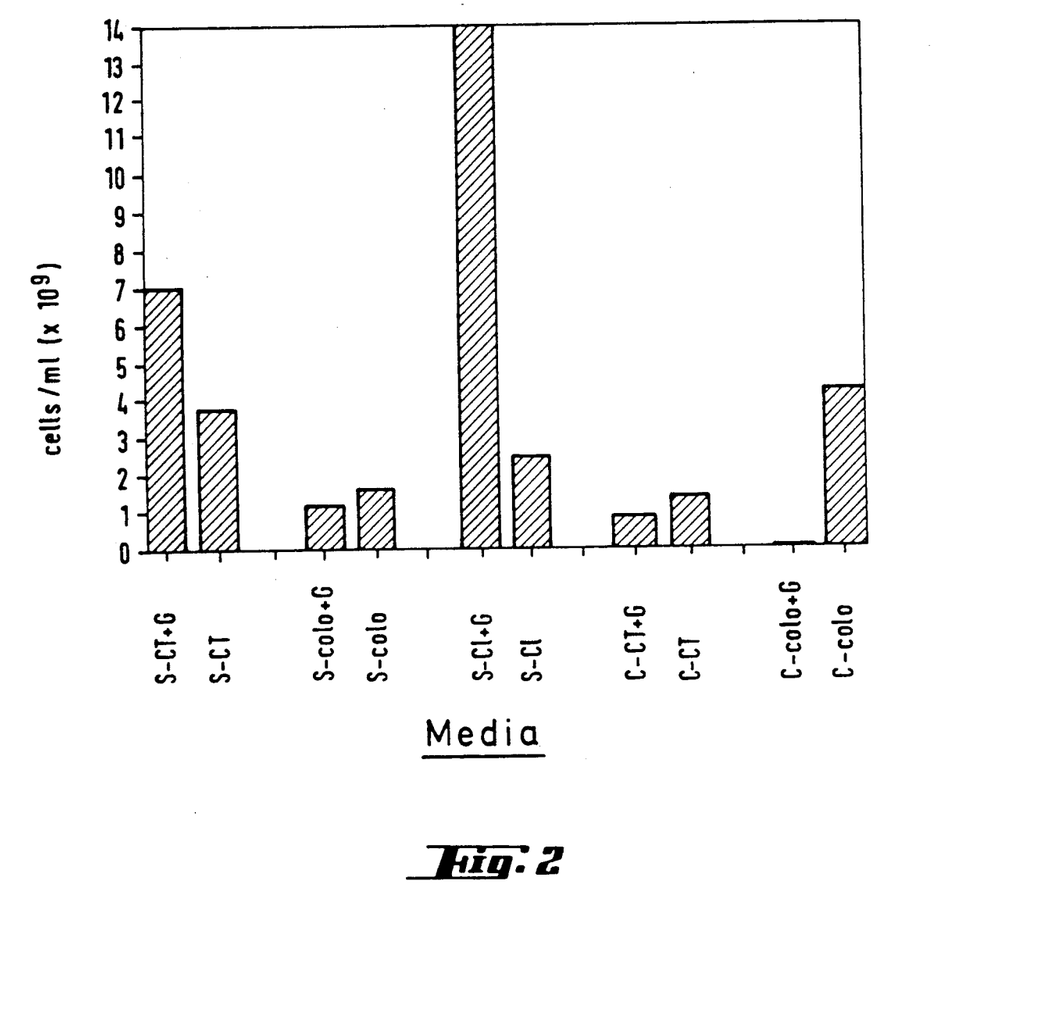

The results clearly show that the S mineral medium is superior to the C mineral medium, both after 6 hours and at 24 hrs of incubation. Additionally, it is clearly seen that from the three chitin sources tested CT is as good or better than COLO, while CL is superior to both.

Crude chitin, which is prepared from a waste product and is therefore the cheapest source of chitin among the three sources, is a preferred chitin source for growing the 20M culture. The superiority of crude chitin may be attributed to the fact that it contains protein residues and perhaps also vitamins and other nutritional components, in contrast to the other two sources which contain very little organic material other than chitin.

When a purer source of chitin is needed, the use of CT is preferred, since in addition to giving rise to better growth, it is also a cheaper source of chitin than COLO, whose preparation is laborious and time consuming.

In the case of the C mineral solution, the effect of 10 glucose supplementation was detrimental. This is probably due to the fact that the C solution medium has a very little buffer capacity whereas the S mineral medium, with a balance between mono- and di-basic potassium phosphate, has a better buffer capacity. Glucose in a fermentation medium lowers the pH, and probably, with the limited buffer capacity of the C medium, the medium became too acidic for bacterial growth, whereas the lowering of the pH was less in the S medium and it still provided suitable growth conditions.

It should be noted however, that whereas after 6 hrs the glucose retarded the growth in the S-CT and S-CL media, this effect was reversed after 24 hours by which time the media with a glucose supplementation, had a much higher cell count than those without glucose. One possible explanation is that the lagtime for these two cultures is different.

(b) The effect of pH

Figure 3:
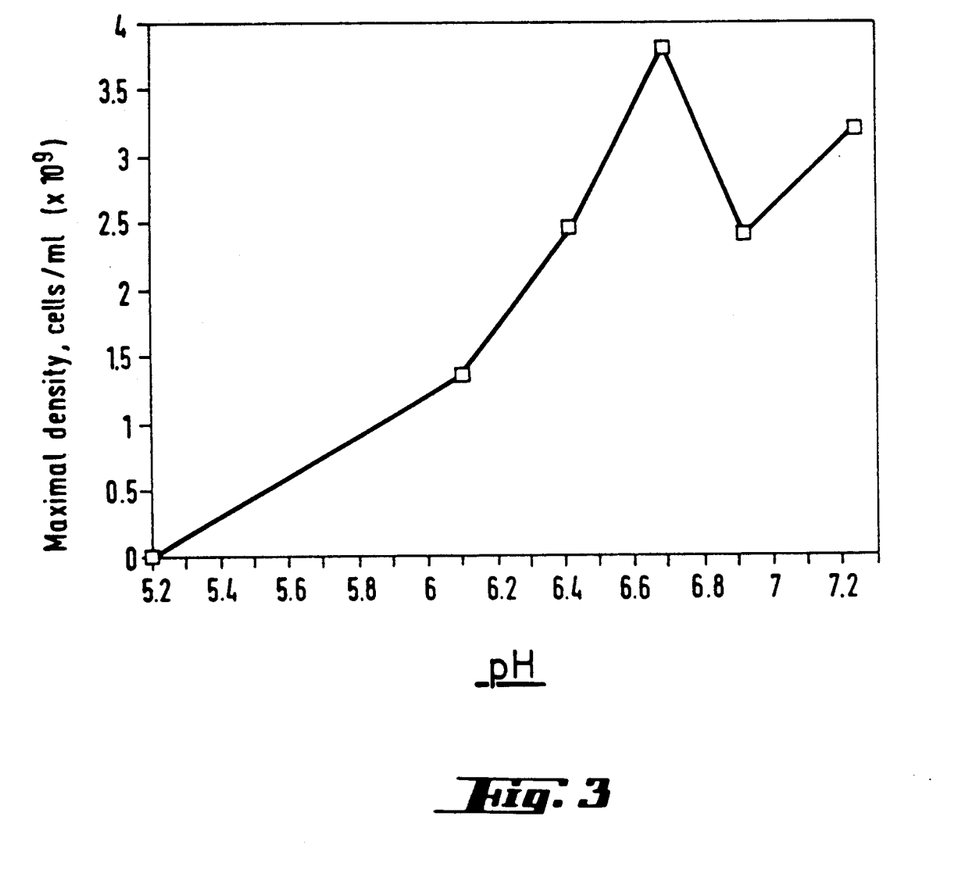
FIG. 3 shows results of an experiment wherein the effect of pH on 20M cell proliferation was tested.

Cultures were grown in an S medium containing colloidal chitin and the pH was manipulated by changing the proportions of mono- and di- basic potassium phosphate. The pH was varied between 5.2 and 7.2, and the results are graphically represented in FIG. 3 of the annexed drawings which shows that the optimal pH for growth of the 20M bacteria in this medium is between 6.4 and 7.2.

This sensitivity to pH explains the differences in growth for the various media tested under a). Media in which pH changes occur beyond the limits of tolerance, will induce less growth than those in which the pH remains within the tolerance levels.

The good growth results achieved with crude chitin as chitin source, may possibly be explained by the fact that it contains proteins and fermentation in a proteinaceous medium tends to raise the pH while fermentation with glucose tends to lower the pH. Apparently, crude chitin and glucose counteract to balance the pH, while at the same time glucose constitutes a good growth medium.

(c) Effect of buffer molarity on 20M growth

Maintenance of optimal pH levels in the medium can in principle also be achieved by strengthening the buffer capacity. In order to test whether the 20M bacteria can tolerate higher salt concentrations needed in order to increase buffer capacity, cell growth was determined with different buffer concentrations while the remaining constituents of the growth medium were left unchanged. The resulting bacterial cell concentration was counted in each case after 24 hrs of aerobic growth.

It was found that while bacteria grew also at high buffer levels, maximum bacterial cell concentration was seen in media where the buffer level was below 0.01 M. These results show that the micro-organisms are sensitive to high salt concentrations and hence the preference, in accordance with the invention that the buffer concentration in the fermentation medium be kept below about 0.01 M.

(d) Effect of yeast extract concentration on 20M growth

Figure 4:
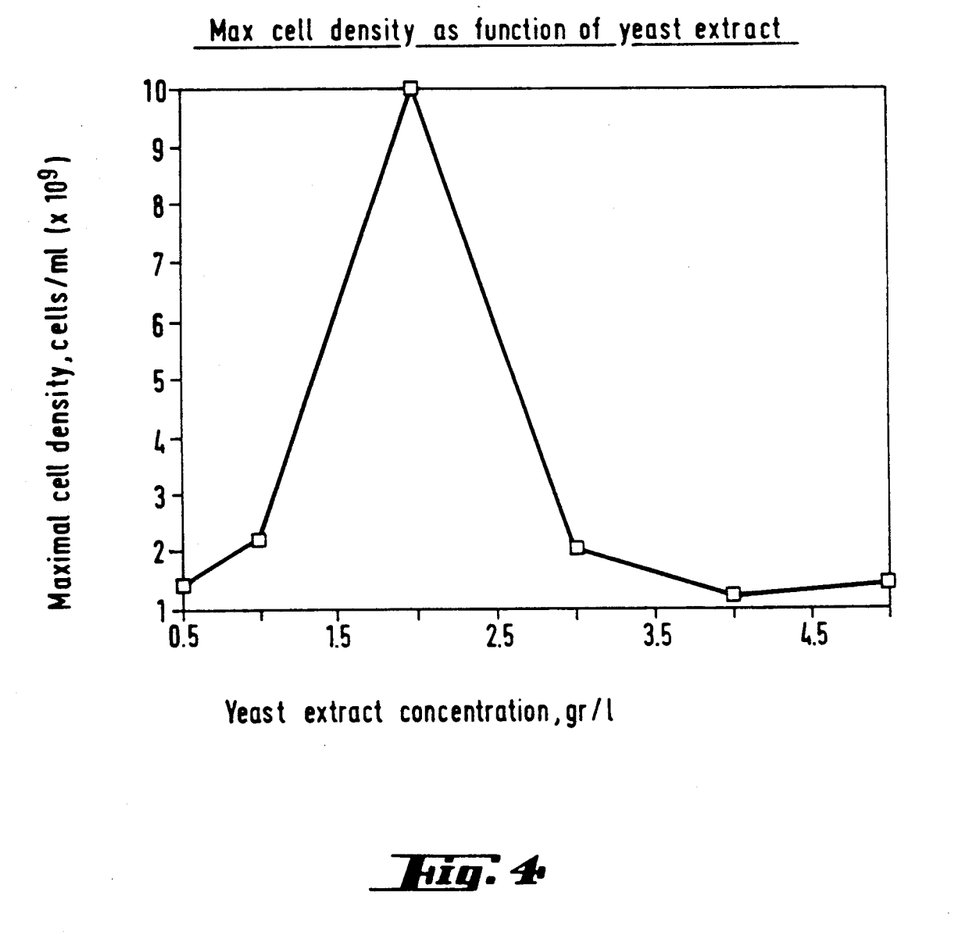
FIG. 4 shows results of a experiment wherein the effect of yeast extract in two different media, on 20M cell proliferation, was tested.

The effect of yeast extract concentration on 20M growth was tested in the S-CL+G and the S-COLO media and the results are graphically represented in FIG. 4.

In the S-COLO medium growth was improved by yeast supplementation with a peak at 2 g/l. However, beyond 3 g/l growth decreased. This decrease may be attributed to the tendency of the yeast extracts supplementation to raise the pH of a medium beyond a tolerance limits.

The optimal amount of yeast extract required might vary with different carbon sources added to the medium.

(e) Effect of ratios of various medium constituents on 20M growth

In formulating a growth medium, nutrients must be provided in balance so that no single factor will become limiting, and the pH and mineral strength will be kept within tolerance limits of bacterial growth. As shown above, yeast extract positively affects growth, but its supplementation to high levels may affect the pH and therefore should be kept within limits. In addition, it was found that glucose enhances growth only when there is no excessively high amount of a nitrogen source in the medium (see below). Possibly, however, if the various supplements were well balanced, e.g. by supplying simultaneously more crude chitin and glucose while maintaining the two in balance, better growth would be achieved. The following experiments were performed in order to test whether changing the ratios between different supplements could improve growth rate.

($e_1$) Effect of crude chitin :glucose ratio on 20M growth

The results are summarized in the following Table III

TABLE III

| | Exp. No. | | | | | | |
|---|---|---|---|---|---|---|---|
| | 1 | 2 | 3 | 4 | 5 | 6 | 7 |
| CL (%)* | 0.1 | 0.1 | 0.2 | 0.2 | 0.2 | 0.4 | 0.4 |
| G (%)* | 0.1 | 0.2 | 0.1 | 0.2 | 0.4 | 0.2 | 0.4 |
| pH** | 7.0 | 6.7 | 7.1 | 6.7 | 5.8 | 7.0 | 6.2 |
| Cell density*** | 4.0 | 5.8 | 5.0 | 5.3 | 4.0 | 5.1 | 10.0 |

*% - w/v
**pH - measured during fermentation
***Cell density - relative concentrations The maximal density of the cells was similar for all the tests with the exception of the medium containing 0.4% of each crude chitin and glucose, in which the maximum cell density was significantly higher. Growth rates were also higher in this latter medium.

These results show that the amounts of crude chitin and glucose may be increased provided their relative ratio is maintained.

($e_2$) The effect of crude chitin, glucose, yeast extract, $KNO_3$ ration on 20M growth rate The concentration of crude chitin, glucose, yeast extracts and $KNO_3$ was changed, the remaining constituents being the same as in Example 2. The growth rate of the 20M culture was determined in each case and the results are summarized in the following Table IV:

TABLE IV

| | Exp. No. | | | | | | | | |
|---|---|---|---|---|---|---|---|---|---|
| | 1 | 2 | 3 | 4 | 5 | 6 | 7 | 8 | 9 |
| CL (%)* | 0.2 | 0.4 | 0.4 | 0.4 | 0.4 | 0.4 | 0.4 | 0.4 | 0.4 |
| G (%)* | 0.2 | 0.2 | 0.2 | 0.2 | 0.2 | 0.4 | 0.4 | 0.4 | 0.4 |
| Ye (%)* | 0.2 | 0.1 | 0.1 | 0.2 | 0.2 | 0.1 | 0.1 | 0.2 | 0.2 |
| $KNO_3$ (g/l) | 1.0 | 0.5 | 1.0 | 0.5 | 1.0 | 0.5 | 1.0 | 0.5 | 1.0 |
| pH** | 6.7 | 6.6 | 6.7 | 7.0 | 6.8 | 6.3 | 4.9 | 5.3 | 5.7 |
| Cell density*** | 3.5 | 3.6 | 3.1 | 10.0 | 4.2 | 3.0 | 0.2 | 1.2 | 2.7 |

*% - w/v
**pH - measured during fermentation
***Cell density - relative concentrations.

In each case 1 g/l $KNO_3$ lowered growth and maximum cell density as compared to 0.5 g/l $KNO_3$. 0.4% Glucose caused acidic conditions and resulted in consistently lower final cell densities, as compared to 0.2% glucose. The addition of yeast extract raised the pH slightly and tended to enhance growth.

In view of the above results, the preferred medium in accordance with the present invention would be the S mineral medium with supplemented 0.1 gm/l $KNO_3$, 0.3% yeast extract, 0.2-0.4% crude chitin as chitin source and 0.2% glucose.

EXAMPLE 8

Nematicidal activity of 20M

Aliquots of 20M packed cells were added to pots containing nematode inoculated soil (500 eggs of *M. javanica* for each pot). $10^8$ cells/g of soil were added prior to planting of tomato seedlings.

The effect of 20M on the plants was evaluated by using several parameters: total top-fresh weight, degree of knot formation in the root and the number of eggs.

The results are shown in the following Table V:

TABLE V

| Exp. | Treatment | Top fresh weight g/plant | Galling Index | No. of eggs/ g/root |
|---|---|---|---|---|
| 1 | Nematode (blank) | 1.53 | 2.50 | 1317.2 |
| | Nematode + 20M | 2.33 | 1.18 | 260.2 |
| 2 | Nematode (blank) | 2.20 | 1.47 | 1777.0 |

TABLE V-continued

| Exp. | Treatment | Top fresh weight g/plant | Galling Index | No. of eggs/ g/root |
|---|---|---|---|---|
| | Nematode + 20M | 3.38 | 0.18 | 178.6 |
| 3 | Nematode (blank) | 2.52 | 2.27 | 6167.5 |
| | Nematode + 20M | 3.86 | 1.43 | 2120.0 |
| 4 | Nematode (blank) | 2.19 | 2.87 | 18007.5 |
| | Nematode + 20M | 3.06 | 1.50 | 1870.0 |

It may be seen from the above results that 20M cause a dramatic inhibition of *M. javanica* propagation and 90% reduction in counts.

Similar results were obtained in nine additional experiments.

EXAMPLE 9

Characterization of the 20M strain

The properties of this strain were determined in accordance with accepted practice and the following results were obtained:

| | | Hydrolysis of: | |
|---|---|---|---|
| Shape of cells | rods | starch | + |
| width um | 0.6–1.0 | gelatin | + |
| length um | 1.5–5.0 | casein | + |
| Motility | + | DNA | no gr |
| Flagellation | polar > 1 | Tween 80 | + |
| Gram reaction | − | esculin | + |
| Lysis by 3% KOH | − | Tyrosine degradation | − |
| Aminopeptidase (Cerny) | + | Growth factor requirement | − |
| Spores | − | Utilization of: | |
| Oxidase | + | acetate | − |
| Catalase | + | adipate | − |
| Growth: | | benzoate | − |
| anaerobic | − | butyrate | − |
| 37/41° C. | +/− | caparate | − |
| pH 5.6 | − | citrate | − |
| Mac-Conkey-Agar | − | citraconate | − |
| SS-Agar | − | fumarate | + |
| Cetrimid-Agar | − | glycolate | − |
| NaCl 3% | − | lactate | − |
| Pigments | yellow | levulinate | − |
| non diffusible | + | malate | − |
| diffusible | − | malonate | − |
| fluorescent | − | phenylacetate | − |
| pyocyanine | − | propionate | − |
| Acid from (OF-Test): | | pyruvate | + |
| glucose aerobic | − | saccharate | + |
| glucose anaerobic | − | succinate | − |
| Gas from glucose | − | L-arabinose | + |
| Acid from (ASS): | | fructose | + |
| arabinose | + | glucose | + |
| cellobiose | + | mannose | + |
| galactose | + | maltose | + |
| glucose | + | L-rhamnose | + |
| fructose | + | ribose | + |
| lactose | − | saccharose | − |
| maltose | + | trihalose | + |
| saccharose | − | xylose | + |
| xylose | + | m-inositol | − |
| ethanol | − | mannitol | − |
| ONPG | − | gluconate | + |
| ADH | − | 2-ketogluconate | − |
| VP | − | N-acetylglucosamine | − |
| Indol | − | L-glutamate | + |
| NO2 from NO3 | − | L-histidine | + |
| Denitrification | − | L-serine | − |
| Phenylalanine deaminase | − | L-threonine | − |
| Levan from sucrose | − | n-butanol | − |
| Lecithinase | − | | |
| Urease | − | | |
| Poly-β-hydroxy-butyrate | + | | |

Cellwell type: A 1γ, meso-DAP direct
Small amounts of meso-DAP were found, which is typical for Gram negative bacteria.

On the basis of the above results it was determined that the strain 20M belongs to the genus *Pseudomonas*. The species of the strain was not yet identified and ti may be a new one.

EXAMPLE 10

Characterization of strain 2F

The following results were obtained:

| Shape | rods | β-galactosidase | + |
|---|---|---|---|
| Motility | + | arginine-dehydrolase | + |
| Growth reaction | − | lysine-decarboxylase | + |
| Spores | − | ornithine-decarboxylase | − |
| Oxidase | − | citrate utilization | − |
| Catalase | − | $H_2S$ production | − |
| Growth: | | urease | − |
| anaerobic | + | tryptophone deaminase | − |
| aerobic | + | Indol production | + |
| NaCl 0% | + | acetone production | +/− |
| 3% | + | (from pyruvic acid) | |
| 7.5% | − | celatinase | + |
| Pigments | − | $NO_2$ production from $NO_3$ | + |
| (op. 100–200 nm) | | reduction to $N_2$ gas | − |

| Hydrolysis of: | | |
|---|---|---|
| starch | + | glucose fermentation | − |
| Tween 80 | + | glucose oxidation | + |
| casein | + | MacConkey medium | + |
| Resistance to the vibriostatic compound 2,4-diamino-6,7-diisopropylpteridine | + | growth (gas from glucose*) | −) |
| Acid from: | | |
| glucose | + | | |
| manitol | + | | |
| inositel | − | | |
| sorbitol | − | | |
| rhammose | − | | |
| sucrose | + | | |
| melibiose | − | | |
| anigdalin | + | | |
| arabinase | − | | |

On the basis of the above results 2F was identified as the species *Aeromonas hydrophyla*, with a probability of 99.9%.

II: Api 20NE Test

The following results were obtained:

| Reduction of NO₃ to NO₂ | + |
|---|---|
| TPP Indole production | − |
| Glucose acidification | + |
| ADH | + |
| Urease | − |
| Aesculin hydrolysis (β-glucosidase) | + |
| Gelatin hydrolysis (protease) | + |
| ONPG (β-galactosidase) | + |
| Assimilation of: | |
| glucose | + |
| arabinose | − |
| mannose | + |
| manitol | + |
| N-acetyl-glucoseamine | + |
| maltose | + |
| gluconate | + |
| coprate | + |
| adipate | − |
| malate | + |
| citrate | + |
| phenylacetate | − |
| oxidase | + |

On the basis of these results 2F is identified as belonging to the genus *Aeromonas* without a clear identification of the species.

III. APi 50CH Test

The results obtained are shown in the following Table VI:

TABLE VI

| | Oxidation | Fermentation | Assimilation |
|---|---|---|---|
| Glycerol | + | + | + |
| Erythritol | − | − | − |
| D-arabinose | − | − | − |
| L-arabinose | − | − | − |
| Ribose | − | + | + |
| D-xylose | − | − | − |
| L-xylose | − | − | − |
| Adomitol | − | − | − |
| P-methyl-xyloside | − | − | − |
| Galactose | + | + | + |
| D-glucose | − | + | + |
| D-fructose | − | + | + |
| D-mannose | − | + | + |
| L-sorbose | − | − | − |
| Rhamnose | − | − | − |
| Dulcitol | − | − | − |
| Imositol | − | − | − |
| Mommitol | − | + | + |
| Sorbitol | − | − | − |
| a Methyl-D-mannoside | − | − | − |
| a Methyl-D-glucoside | − | + | − |
| N-acetyl-glucosamine | − | + | + |
| Amygdaline | − | − | − |
| Arbutine | − | + | − |
| Esculine | + | + | − |
| Salicine | − | + | − |
| Cellobiose | − | − | − |
| Maltose | − | + | + |
| Lactose | − | − | − |
| Melibiose | − | − | − |
| Saccharose | − | + | + |
| Trihalose | − | + | + |
| Inuline | − | − | − |
| Melezitose | − | − | − |
| D-raffinose | − | − | − |
| Pimidon | − | + | + |
| Glycogene | − | + | + |
| Xylitol | − | − | − |
| β-gentiobiose | − | − | − |
| D-turanose | +/− | − | + |
| D-lyxose | − | − | − |
| D-sagatose | − | − | − |
| D-fructose | − | − | − |
| L-fucose | − | − | − |
| D-arabitol | − | − | − |
| L-arabitol | − | − | − |
| Gluconate | − | + | − |
| 2 ceto-gluconate | − | − | − |
| 5-ceto-gluconate | − | − | − |

On the basis of this test 2F is identified as belonging to the genus *Aeromonas* without a clear indication of the species.

EXAMPLE 11

Nematicidal effect of 2F

Tomato seedlings were planted into pots or styrofoam coneshape cups which contained soil innoculated with nematodes (500 eggs of *M. Javanica* per pot and 100 eggs per cup). Before planting the soil received also one of the following treatments:

(a) no treatment;
(b) addition of chitin 0.05%;
(c) addition of chitin +20M packed cells;
(d) addition of chitin +2F packed cells;
(e) addition of chitin +20M +2F packed cells.

The plants from the styrofoam cups were harvested 7 days after planting and the plants in the pots were harvested 35 days after planting. The amount of larvae per root of the plant in the styrofoam cup and the Galling index (GI) in the pots were determined and the results are presented in FIGS. 5 and 6.

Figure 5:
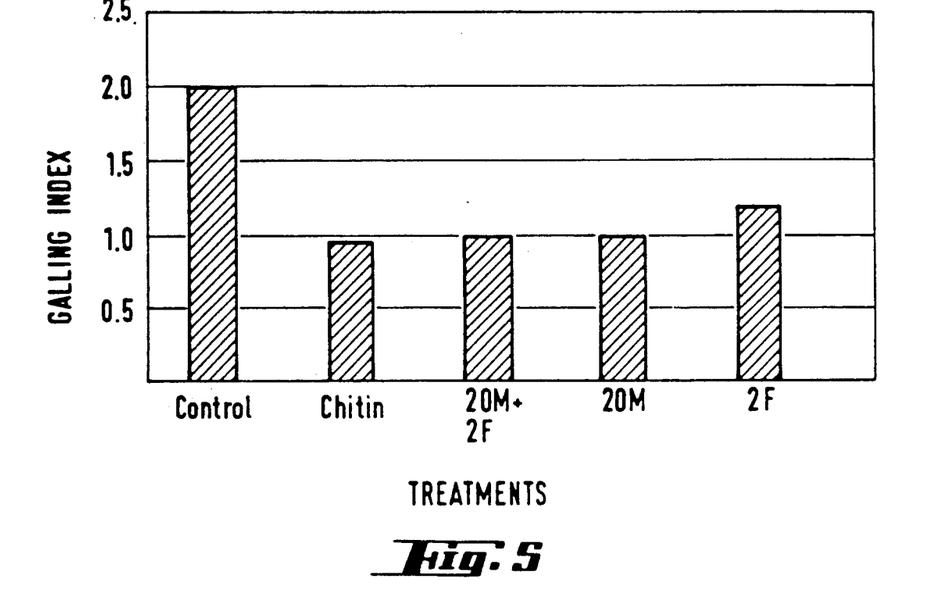
FIG. 5 shows results of an experiment wherein the effect of chitin, 20M and 20F on the Galling Index in roots of tomato plants was tested.
Figure 6:
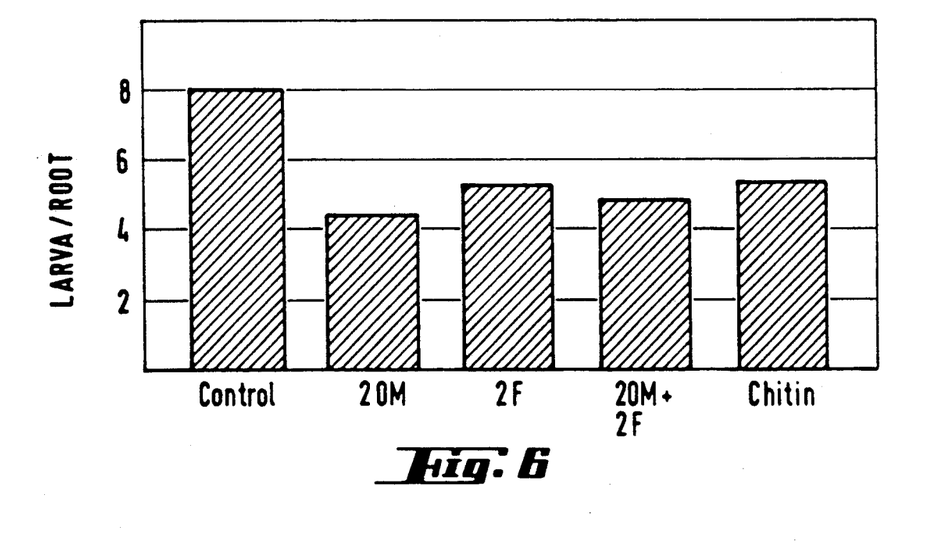
FIG. 6 shows results of an experiment wherein the effect of chitin, 20M and 2F on the numbers of the nematode's larvae per root of tomato plants was tested.

It may be seen that chitin by itself was effective in controlling the nematode infection, presumably by initiating proliferation of chitinolytic micro-organisms present in the soil.

The results also show that 2F and 20M possess nematicidal activity and have a similar effect.

EXAMPLE 12

Isolation of 30CE

The strain 30CE of the species *Cunninghamella elegans* (Mucorales) was isolated from a sandy soil amended with collagen and purified in a Martin-Rose Bengal medium.

Samples of 10 g of the soil were suspended in 90 ml sterile water in 250 ml flasks, which were then shaken for 30 minutes. Decimal dilutions of the suspensions were then prepared and a sample of each dilution was then spread on an agar substrate prepared with a salt medium containing 0.1% collagen, contained in a culturing plate.

The plates were incubated for some time until substantial growth of fungal cells occurred and thereafter samples were transferred to a new agar substrate, and the incubation-transfer cycle was repeated several times until a homogeneous culture was opted.

EXAMPLE 14

Growth medium for 30CE

A suitable medium for growing the 30CE culture has the following composition:

0.2% collagen;
0.08% $K_2HPO_4$;
0.09% $CaCl_2$;
0.039% $MgSO_4.7H_2O$;
0.2% glucose.

In this medium the optimal pH was found to be about 6.5-7 and the optimal temperature was found to be about 30° C.

EXAMPLE 14

Fermentation medium for 30CE

A suitable medium for the fermentation of 30CE comprises about 20% potato broth and about 0.1% collagen.

EXAMPLE 15

Nematicidal activity of 30CE or its residual medium

30CE cultures were added into the growth medium of Example 13 and incubated at 30° C. in shaken Erlenmeyer flasks for 3 days. Either the medium with the fungal cells per se (hereinafter "medium"), or an homogenized medium (hereinafter "homogenate") were then tested.

Each of a plurality of pots containing 500 g of soil inoculated with 650 eggs per pot, were supplemented with either the medium, the filtrate or the homogenate. In some cases also collagen was supplemented to the soil either in addition to the aforementioned supplements, by itself or in combination with chitin.

After 5 weeks the plants were pulled and the roots were observed for root knots and the Galling Index determined. In some cases a nematode count was made. Nematode inoculated, but untreated pots served as controls.

(a) Nematicidal effect of 30CE medium and homogenates

Figure 7:
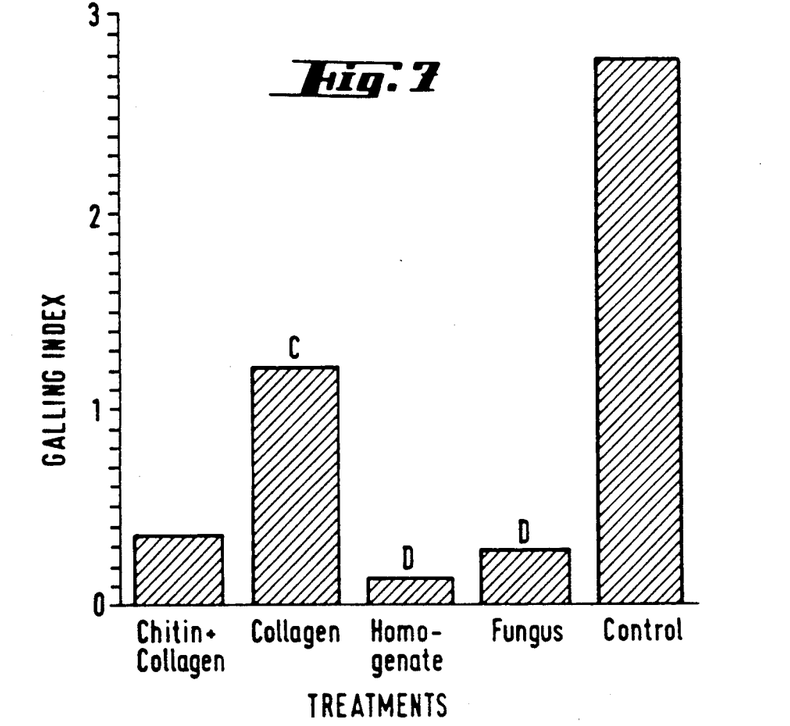
FIG. 7 shows results of an experiment wherein the effect of 30CE, an homogenate thereof, collagen and chitin collagen on the Galling Index was tested.

The effect of various treatments on the Galling Index (GI) is shown in FIG. 7 of the annexed drawings. As can be seen, the homogenate of 30CE had the strongest effect in reducing GI. A similarly strong effect, and not significantly different statistically from the former, was observed when treating the soil with the medium (containing live 30CE cells) and with a mixture of chitin and collagen (the latter effect stems presumably from initiation of proliferation of collagenolytic and chitinolytic micro-organisms in the soil). Some effect was also observed upon treatment with collagen.

(b) Effect on the addition of collagen on the nematicidal activity of 30CE

Figure 8:
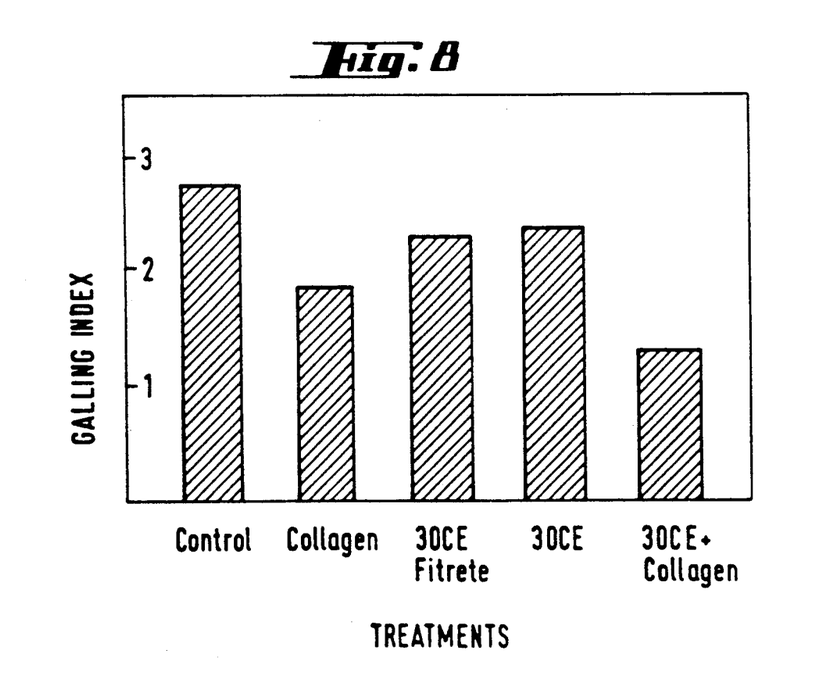
FIG. 8 shows results of an experiment wherein the effect of 30CE with and without collagen on the Galling Index was tested.

As may be seen in FIG. 8 of the annexed drawings, supplementing of 30CE into the soil had some effect in reducing the Galling Index while a much stronger effect was observed when the 30CE culture was supplemented with collagen. Such collagen supplementation enables an enhanced proliferation of the fungal cells.

It should be noted that 30CE was supplemented to the soil in an unformulated form and a much stronger effect, comparable to that obtained with collagen or even more, is expected if 30CE will be appropriately formulated.

We claim:

1. A method of combating soil nematodes comprising introducing into the soil a composition comprising nematicidally effective amount of a biologically pure culture of *Pseudomonas chitinolytica* 20M, CNCM-I-804, or a neumaticidally active mutant thereof.

2. A nematicidal composition for use in plant protection, comprising a biologically pure culture of *Pseudomonas chitinolytica*, 20M, CNCM-I-804, or a nematicidally active mutant thereof, together with a carrier compatible with said bacteria and with soil environment.

3. A composition according to claim 2, comprising an aqueous liquid carrier and said *Pseudomonas chitinolytica* suspended therein.

4. A composition according to claim 2, wherein the carrier is a solid porous material and said *Pseudomonas chitinolytica* are impregnated therein.

5. A composition according to claim 4, further comprising additives that serve as adherents.

6. A composition according to claim 2, further comprising a nutrient source.

7. A composition according to claim 6, wherein the nutrient source is selected from the group consisting of cotton-seed meal, chitin and collagen.

8. A method for preparing a nematicidal composition according to claim 2, comprising admixing to an aqueous suspension which contains a biologically pure culture of *Pseudomonas chitinolytica*, 20M, CNCM-I-804, or a nematicidally active mutant thereof.

9. A biologically pure culture of *Pseudomona chitinolytica* 20M, CNCM-I-804, or nematicidally active mutants thereof.

* * * * *